United States Patent [19] [11] 4,349,020
Krikorian [45] Sep. 14, 1982

[54] SHIRRED LAMINATE

[76] Inventor: William G. Krikorian, Lot #12, Old Dunstable Rd., Groton, Mass. 01450

[21] Appl. No.: 75,398

[22] Filed: Sep. 14, 1979

[51] Int. Cl.³ ............................................. A61F 13/00
[52] U.S. Cl. .................................... 128/155; 128/156
[58] Field of Search ................ 3/1; 128/155, 156, 284

[56] References Cited
U.S. PATENT DOCUMENTS 3,122,142 2/1964 Crowe ................................. 128/156
3,842,832 10/1974 Wideman et al. .................... 128/156
4,146,027 3/1979 Hoey .................................. 128/156

Primary Examiner—Kyle L. Howell
Assistant Examiner—T. J. Wallen
Attorney, Agent, or Firm—E. Thorpe Barrett

[57] ABSTRACT

A laminate consists of two layers of non-woven elastic foam enclosing a non-elastic scrim formed by treating all of the materials with a latex solution, combining the materials under pressure while the two layers of elastic foam are in stretched condition, allowing the material to retract and slitting the material lengthwise into bandage material.

12 Claims, 6 Drawing Figures

SHIRRED LAMINATE

This invention relates to an expandable laminate material that is suitable for various applications, but is particularly directed toward an improved bandage material for use in the veterinarian and human fields of medicine.

Many forms of stretchable material have been devised for use in bandages and other applications. Corrugated or shirred fabrics have been known for many years and have found increasing acceptance in recent times. Many such fabrics are formed by bonding two layers to opposite sides of stretched rubber yarns and then allowing the material to retract causing a puckering or gathering of the material. Another type of material, for example as described in U.S. Pat. No. 3,575,782 to Hanson, issued Apr. 20, 1971, is formed from a series of spaced parallel elastic yarns bonded, while stretched, to two exterior layers of non-woven web material. Such material has found extensive use in bandages because the bandage may be stretched while applying to the elastic limits of the yarns to apply continuing pressure to the bandaged area.

Another material that also finds application in bandages is described in U.S. Pat. No. 3,842,832 to Wideman, issued Oct. 22, 1974, in which an inner layer of cellular foamed plastic material is bonded between layers of non-woven fabric material while the inner layer is under tension.

These and other bandage materials represented a substantial improvement over earlier cloth bandages, and the present invention represents a substantial improvement over the stretch bandages heretofore in use.

It is thus an object of this invention to provide an improved elastic laminate particularly suitable for use in bandages for both human and animal use.

It is a further object of the invention to provide such an improved laminate that is self-adhering and porous.

It is another object to provide a bandage formed from such a laminate with improved tear strength in the longitudinal direction of the bandage.

It is yet another object of the invention to provide such a bandage having a finite limit of stretch in the longitudinal direction, so that failures caused by overstretching are eliminated, and having minimal stretch and necking down in the transverse direction.

It is another object to provide an improved method of making such a bandage that results in lower costs and improved quality.

These and other objects will be in part apparent from, and in part pointed out in, the following description of a preferred embodiment of the invention considered in conjunction with the accompanying drawings, in which.

Figure 1:
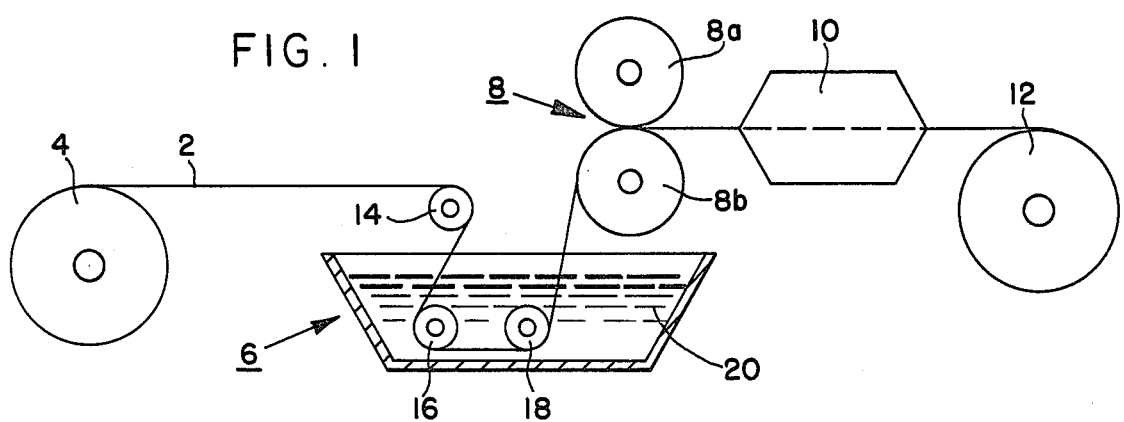
FIG. 1 illustrates the application of an adhesive coating to the individual layers of the laminate material prior to the assembly.

Before assembling the bandage, it is preferred that the three layers of material be treated with latex and dried. FIG. 1 illustrates the method of applying the coating. Polyester foam sheet material 2 from a roll 4 is arranged to be passed through a bath 6 of latex solution, through a pair of wringer rolls 8, and through a drying oven 10, after which it is rewound into a roll 12.

The polyester foam material 2 is preferably an open cell structure with 40 to 45 cells per linear inch and having thickness of about 0.03 in. Such a foam material is available from Tenneco, Inc., Paramus, N.J., and from other sources. The material is passed over a guide roller 14 into the bath 6 and under two rollers 16 and 18 that are submerged in a latex solution 20. The latex solution is formed at 80 percent natural latex and 20 percent synthetic latex. Material sold by Glennon-American Inc., 40 School Street, Middleton, Mass., as #1799 latex saturant is satisfactory for this purpose. The wringer rolls 8a and 8b, which are preferably positioned so that as excess latex solution is squeezed from the foam it returns to the bath 6, are adjusted with sufficient pressure that the latex remaining on the foam is about 0.08 ounces of the latex solution per square yard of foam. The speed and pressure of the rolls should be adjusted to give the desired coating depending upon the characteristics of the particular latex solution being used and the characteristics of the foam. The foam then passes through a drying oven, which removes the water from the latex solution, and onto a supply roll 12.

The central layer 22 of the bandage is formed of a non-elastic scrim, such as cheesecloth, which has perpendicular spaced yarns. I prefer that the material from which the cheesecloth is made be less absorbent than cotton and one that provides greater strength. Polyester cheesecloth with 20 yarns per inch in each direction is suitable. Polypropylene netting with 8×8 yarns per inch, such as is sold by Hercules Inc., Wilmington, Del. under the trademark "Delnet", is also a suitable material. For best results, the density of yarns extending in the machine direction (lengthwise), prior to the formation of the bandage, is greater than the density of the yarns that extend across the material. Preferably, the yarns running in the machine direction are from 8 to 28 per inch, and the cross yarns are between 4 and 20 per inch. The cheesecloth 22 also is treated with a latex solution. The method of applying the latex may be exactly the same as that described in connection with the foam except that the wringers 8 are adjusted so that the wet weight of latex remaining on the scrim after passing through the wringers and before drying is about 0.60 ounces per square yard.

In treating both the scrim and the foam with latex, it is preferred that the wet weight of the latex be equal to at least one-half the weight of the substrate and that it should not exceed the weight of the substrate. Proper choice of the latex used will result in a porous laminate which is desirable in bandages and for other uses. Where little or no porosity is desired, greater amounts of latex may be applied.

Figure 2:
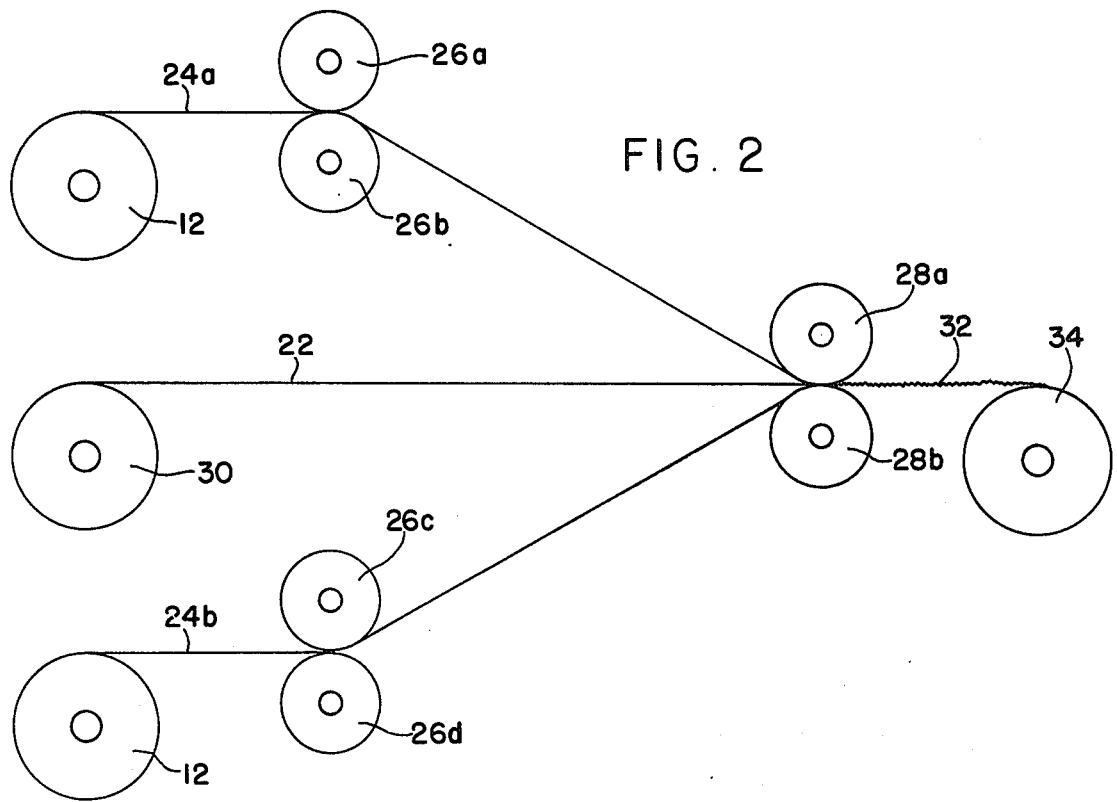
FIG. 2 illustrates the laminating of the three layers into a single layer of shirred material.

To form the bandage, the polyester foam, indicated at 24a and 24b in FIG. 2, which has been treated with the latex solution and dried, is fed from the supply roll 12 through a pair of nip rolls 26a and 26b and then between a pair of pressure rolls 28a and 28b. Another supply roll 12 of the treated polyester foam, as indicated at 24b, is fed through the a similar pair of nip rolls 26c and 26d and then between the pressure rolls 28a and 28b.

The scrim 22, which has been treated with the latex solution and dried, is fed from a supply roll into the pressure rolls 28a and 28b between the two layers 24a and 24b of foam.

The foam material 24a and 24b is in stretched condition when it is laminated with the layer of scrim. This is accomplished by adjusting the relative speeds of the nip rolls and the pressure rolls. In this example, the nip rolls 26a and 26b have a peripheral speed equal to one third the peripheral speed of the pressure rolls 28a and 28b. The nip rolls 26c and 26d are driven at the same speed as the rolls 26a and 26b. With this arrangement, the two pairs of nip rolls serve as brakes that hold back the foam material so that it is in stretched condition at the time it is pressed into a unit laminate with the scrim 22. As the laminated material, indicated at 32, leaves the pressure rolls 28a and 28b, the elastic foam retracts to approximately its original length, causing the scrim to pucker so that the completed bandage will have a slightly rough or crinkled appearance. The inner layer of scrim 22 of the material 32 when in the relaxed condition is puckered, by which is meant that the yarns in the direction the material moves through the rolls are crinkled forming a generally undulating, corrugated or ruffled pattern. When the material 32 is stretched, for example to double or triple its original length, the inner layer reaches, at the full extension, its full length and effectively prevents further stretching of the material. The material 32 is fed onto a roll 34 in preparation for the slitting operation.

Figure 3:
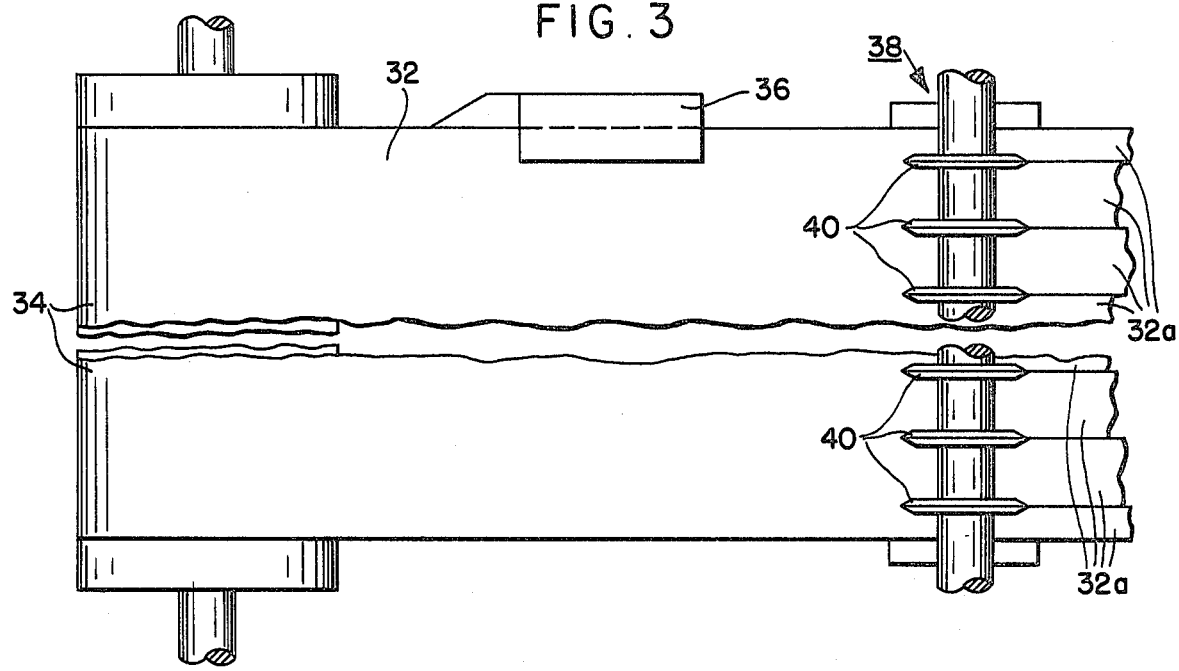
FIG. 3 illustrates the separation of a wide width of laminate into a number of separate bandages.

The slitting operation is indicated in FIG. 3. The roll 34 of bandage material is fed through an edge control mechanism 36, which positions one edge of the material, into a conventional slitter 38 equipped with spaced slitting knives 40 that cut the material 32 into individual bandages as indicated at 32a. Because of the elastic nature of the material, it is difficult to control accurately the width of the laminate during its manufacture and it is desirable therefore to fabricate the laminate in relatively wide widths to minimize waste when the laminate is slit. In addition, if the cross yarns are spaced closely together and it is attempted to slit near the edge of the material 32, the edge will have a ragged appearance. It is desirable therefore to leave as much as one-half inch of material as waste on each side. As a practical matter, a width of 48 or 80 inches is desirable to minimize the waste produced by slitting.

Figure 4:
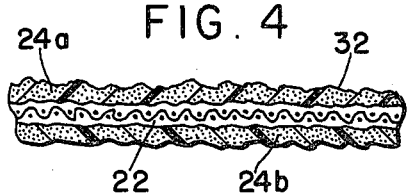
FIG. 4 is an enlarged diagrammatic cross-sectional representation of the laminate when in relaxed condition.

FIG. 4 shows a cross-section of the material 32 as it appears in a relaxed condition. The scrim material is readily confined between the layers of elastic foam 24a and 24b provided the cross yarns are close enough together. If too few cross yarns per inch are used, the cross yarns may penetrate the foam material to form individual loops extending above the surface of the bandage. If the scrim is formed of monofilament material, these loops cause the bandage to have an undesirably rough surface. In practice, the scrim should be selected with as low a number of cross yarns per inch as possible without producing an undesirably rough bandage. Fewer yarns per inch result in a smoother edge cut when the bandages are formed by slitting, particularly if the slit is made near an edge of the material 32.

Figure 5:
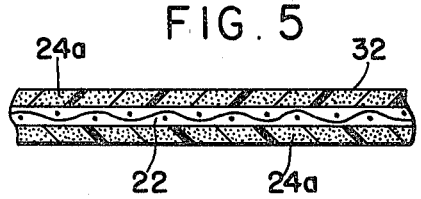
FIG. 5 is a similar representation when the laminate is in stretched condition.
Figure 6:
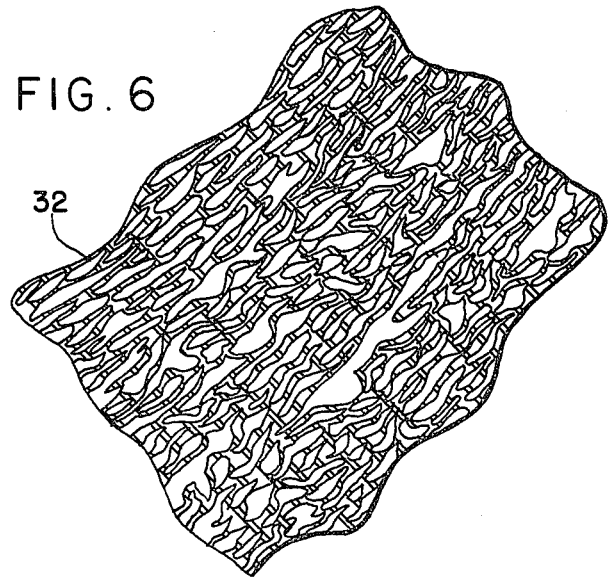
FIG. 6 is an illustration of the magnified surface of the laminate showing the porosity.

When the bandage is stretched, the elastic foam is elongated and the puckers disappear from the scrim, as indicated in FIG. 5. When the bandage has been stretched to the point where the non-elastic scrim is fully extended, the bandage resists further extension, which can occur only if the scrim is torn.

The finished bandage thus meets the most rigid requirements for both animal and human applications. The bandage may readily be fabricated to have a permitted stretch factor of 100%, and strength sufficient for any practical application. The strength is exhibited in both directions and the necking down is minimal even under the fully stretched condition.

The bandage as described with three layers is both strong and durable and is suitable for the most demanding applications. A lighter and less durable bandage, having application in less demanding situations can be constructed with two layers of material. Thus, by eliminating the layer 24b of elastic polymer and using only the elastic layer 24a and the layer 22 of scrim, an acceptable bandage for limited applications can be fabricated.

From the foregoing it will be apparent that the laminate embodying my invention is well adapted to meet the ends and objects set forth herein and is suitable for a wide variety of purposes in the form described here. It will be seen also that the characteristics of the laminate can be readily altered to best fit it for each particular application.

I claim:

1. A self-adhesive bandage for wrapping and maintaining support for animal or human limbs comprising first and second strips of stretchable elastic polymer, a third strip of puckered non-elastic scrim formed of a first set of substantially parallel yarns and a second set of substantially parallel yarns extending at an angle to the yarns of said first set, and elastic adhesive material binding said strips in face-to-face relationship with said first and second strips on opposite sides of said third strip forming a bandage structure capable of being stretched to a predetermined length limited by said non-elastic scrim.

2. An elastic laminate as claimed in claim 1 wherein said elastic polymer is non-woven plastic foam.

3. An elastic laminate as claimed in claim 1 wherein said elastic polymer is polyurethane foam.

4. An elastic laminate as claimed in claim 1 wherein said elastic polymer is a polyester foam having an open cell structure.

5. An elastic laminate as claimed in claim 4 wherein said foam has about 40 to 45 cells per linear inch and a thickness of about 0.03 inches.

6. An elastic laminate as claimed in claim 1 wherein said adhesive is latex.

7. An elastic laminate as claimed in claim 6 wherein said latex is a mixture of natural and synthetic latex.

8. An elastic laminate as claimed in claim 7 wherein said latex is about 80% natural latex and about 20% synthetic latex.

9. An elastic laminate as claimed in claim 1 wherein said third layer is formed of a first set of yarns spaced between 8 and 28 yarns per inch and a second set of yarns spaced between 4 and 20 per inch.

10. An elastic laminate as claimed in claim 1 wherein said third layer is formed of a non-absorbent netting of monofilament yarns extending in perpendicular directions.

11. An elastic laminate as claimed in claim 10 wherein said netting is formed of polypropylene.

12. An elastic laminate as claimed in claim 10 wherein said netting is formed of polyester cheesecloth having about 20 yarns per inch in each direction.

* * * * *